United States Patent
Soscia et al.

(10) Patent No.: US 9,909,093 B2
(45) Date of Patent: Mar. 6, 2018

(54) FUNNEL FOR LOCALIZING BIOLOGICAL CELL PLACEMENT AND ARRANGEMENT

(71) Applicant: Lawrence Livermore National Security, LLC, Livermore, CA (US)

(72) Inventors: David Soscia, Livermore, CA (US); William J. Benett, Livermore, CA (US); Erik V. Mukerjee, Dublin, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 138 days.

(21) Appl. No.: 14/824,857

(22) Filed: Aug. 12, 2015

(65) Prior Publication Data

US 2017/0044482 A1    Feb. 16, 2017

(51) Int. Cl.
*C12M 1/00*    (2006.01)
*C12M 3/00*    (2006.01)
*C12M 1/26*    (2006.01)

(52) U.S. Cl.
CPC ............ *C12M 33/00* (2013.01); *C12M 23/40* (2013.01)

(58) Field of Classification Search
CPC ......... C12N 1/00; C12M 23/40; C12M 33/00; B01L 3/56
See application file for complete search history.

(56) References Cited

U.S. PATENT DOCUMENTS

| | | | | |
|---|---|---|---|---|
| 2003/0073228 A1* | 4/2003 | Duffy | ........................ | G06T 7/70 435/287.1 |
| 2004/0214313 A1* | 10/2004 | Zhang | .................... | C12M 23/10 435/288.4 |
| 2004/0229349 A1* | 11/2004 | Daridon | .................... | C12M 1/34 435/305.2 |
| 2011/0199187 A1* | 8/2011 | Davidowitz | ............ | B01L 3/545 340/10.1 |
| 2014/0286836 A1* | 9/2014 | Clavaguera | .......... | G01N 1/2205 422/535 |
| 2016/0250393 A1* | 9/2016 | Jeong | ...................... | A61L 27/54 424/425 |

(Continued)

FOREIGN PATENT DOCUMENTS

WO    WO-2015111722 A1 *   7/2015

OTHER PUBLICATIONS

Rettig, Jacqueline R. et al. "Large-Scale Single-Cell Trapping and Imaging Using Microwell Arrays," Analytical Chemistry, vol. 77, No. 17 (2005), pp. 5628-5634.

(Continued)

*Primary Examiner* — Nathan A Bowers
(74) *Attorney, Agent, or Firm* — Harness, Dickey & Pierce, P.L.C.

(57) ABSTRACT

The present disclosure relates to a funnel apparatus for channeling cells onto a plurality of distinct, closely spaced regions of a seeding surface. The funnel apparatus has a body portion having an upper surface and a lower surface. The body portion forms a plurality of flow paths, at least one of which is shaped to have a decreasing cross-sectional area from the upper surface to the lower surface. The flow paths are formed at the lower surface to enable cells deposited into the flow paths at the upper surface of the funnel apparatus to be channeled into a plurality of distinct, closely spaced regions on the seeding surface positioned adjacent the lower surface.

18 Claims, 6 Drawing Sheets

(56) References Cited

U.S. PATENT DOCUMENTS

2017/0002315 A1* 1/2017 Urisu .................. C12M 25/06

OTHER PUBLICATIONS

Mohr, Jeffrey C. et al. "3-D Microwell Culture of Human Embryonic Stem Cells," Biomaterials, vol. 27, No. 36 (2006), pp. 6032-6042.

Ostuni, Emanuele et al. "Patterning Mammalian Cells Using Elastomeric Membranes," Langmuir, vol. 16, No. 20 (2000), pp. 7811-7819.

Kane, Ravi S. et al. "Patterning Proteins and Cells Using Soft Lithography," Biomaterials, vol. 20, No. 23, (1999), pp. 2363-2376.

* cited by examiner

FUNNEL FOR LOCALIZING BIOLOGICAL CELL PLACEMENT AND ARRANGEMENT

STATEMENT OF GOVERNMENT RIGHTS

The United States Government has rights in this invention pursuant to Contract No. DE-AC52-07NA27344 between the U.S. Department of Energy and Lawrence Livermore National Security, LLC, for the operation of Lawrence Livermore National Laboratory.

FIELD

The present disclosure relates to systems and methods for seeding cells, or groups of cells, onto a growth surface, and more particularly to a funnel-like apparatus which allows cells, or groups of cells, to be deposited through macroscale openings at an upper end of the device, and to be channeled to specific, predetermined regions of a growth surface, possibly separated by distances on the order of microns, without the use of chemical modifications or permanent physical modifications to the growth surface.

BACKGROUND

This section provides background information related to the present disclosure which is not necessarily prior art.

A current limitation in biology, biomedical engineering, and related fields is an inability during seeding on a growth surface to segregate populations of varying cell types, as well as selectively placing cells only in specific areas, without the use of chemical or permanent physical surface modifications.

Using arrays of micropatterned wells, groups have been able to separate individual cells into physical compartments (see, e.g., Jacqueline R. Rettig and Albert Folch, *Large-Scale Single-Cell Trapping And Imaging Using Microwell Arrays*, Analytical Chemistry, 77 (17), 2005, 5628-5634) or several cells into physical compartments (see, e.g., Jeffrey C. Mohr, Juan J. de Pablo, Sean P. Palecek, *3-D Microwell Culture of Human Embryonic Stem Cells*, Biomaterials, 27 (36), 2006, 6032-6042). These methods are beneficial in that they are capable of separating cells into very small populations, however they have no means of sorting different types of cells into specific wells. And since the wells "trap" the cells within physical barriers, growth and motility of the cells are restricted.

A more improved version of this technology uses micropatterned "holes" in Polydimethylsiloxane (PDMS) or another elastomeric polymer, which is laid on top of a growth substrate before cell seeding. The cells are deposited onto the array of holes such that they land and attach on the substrate, then the PDMS hole array is removed, leaving the cells patterned only in areas where the holes extended to the substrate (see, Emanuele Ostuni, Ravi Kane, Christopher S. Chen, Donald E. Ingber, and, and George M. Whitesides, *Patterning Mammalian Cells Using Elastomeric Membranes*, Langmuir 16 (20), 2000, 7811-7819). This allows the cells to grow freely on an unconfined surface, however it does not provide a means for seeding multiple cell types simultaneously. Other groups have used microcontact printing and other methods to pattern cell-adhesive chemicals and proteins onto substrates, causing cells to only attach to those regions containing the chemical (see Ravi S Kane, Shuichi Takayama, Emanuele Ostuni, Donald E Ingber, George M Whitesides, *Patterning Proteins and Cells Using Soft Lithography*, Biomaterials, 20 (23-24), 1999, 2363-2376). Though this allows cells to grow freely on a flat surface, the surface has been modified chemically in specific areas, causing potential variation in how the cell population grows, migrates, and proliferates. It is possible to have different cell types attach to certain areas by patterning chemicals that interact preferentially with certain cells. However, many of the chemicals or proteins used in this approach interact favorably with many types of cells. This is especially true if the cell populations used are from the same organ (e.g., the brain or spinal cord).

This invention addresses all of the aforementioned shortcomings in a relatively simple and easy to use design. The proposed funnel design allows for multiple cell types to easily be seeded into macroscale openings at the top of the device, then the openings narrow substantially such that the cells land on the surface separated by distances as small as several microns. Once the cells attach, the funnel is removed, producing a flat, unmodified surface with cells of one or more types localized to specific regions of the substrate.

SUMMARY

This section provides a general summary of the disclosure, and is not a comprehensive disclosure of its full scope or all of its features.

In one aspect the present disclosure relates to a funnel apparatus for channeling cells onto a plurality of distinct, closely spaced regions of a seeding surface. The funnel apparatus comprises a body portion having an upper surface and a lower surface. The body portion forms a plurality of flow paths, at least one of which is shaped to have a decreasing cross-sectional area from the upper surface to the lower surface. The flow paths are formed at the lower surface to enable cells deposited into the flow paths at the upper surface of the funnel apparatus to be channeled into a plurality of distinct, closely spaced regions on the seeding surface positioned adjacent the lower surface.

In another aspect the present disclosure relates to a funnel apparatus for channeling cells onto a plurality of distinct, closely spaced regions of a seeding surface. The funnel apparatus may comprise an upper funnel having a body portion, the body portion having an upper surface and a lower surface. The body portion may form a plurality of flow paths, at least one of which is shaped to have a decreasing cross-sectional area from the upper surface to the lower surface. A lower funnel may be included which has a body portion having an upper surface and a lower surface. The body portion of the lower funnel may be positioned such that the upper surface of the lower funnel rests against the lower surface of the upper funnel. The lower funnel may also include an additional plurality of flow paths in registration with the plurality of flow paths of the upper funnel, such that cells deposited into the plurality of flow paths of the upper funnel flow through the additional plurality of flow paths of the lower funnel and onto predetermined regions of the seeding surface placed adjacent the lower surface of the lower funnel.

In still another aspect the present disclosure comprises a method for channeling cells onto a plurality of closely spaced apart regions of a seeding surface. The method may comprise arranging an upper funnel having a first plurality of flow paths of decreasing cross sectional area above the seeding surface. The method may also comprise arranging a lower funnel having a second plurality of flow paths which are in registration with the first plurality of flow paths, below the upper funnel and above the seeding surface. The method may further comprise using the upper and lower funnels to channel cells deposited into the first plurality of flow paths onto spaced apart, predetermined regions of the seeding surface.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure. In the drawings.

Corresponding reference numerals indicate corresponding parts throughout the several views of the drawings.

DETAILED DESCRIPTION

Example embodiments will now be described more fully with reference to the accompanying drawings.

Figure 1A:
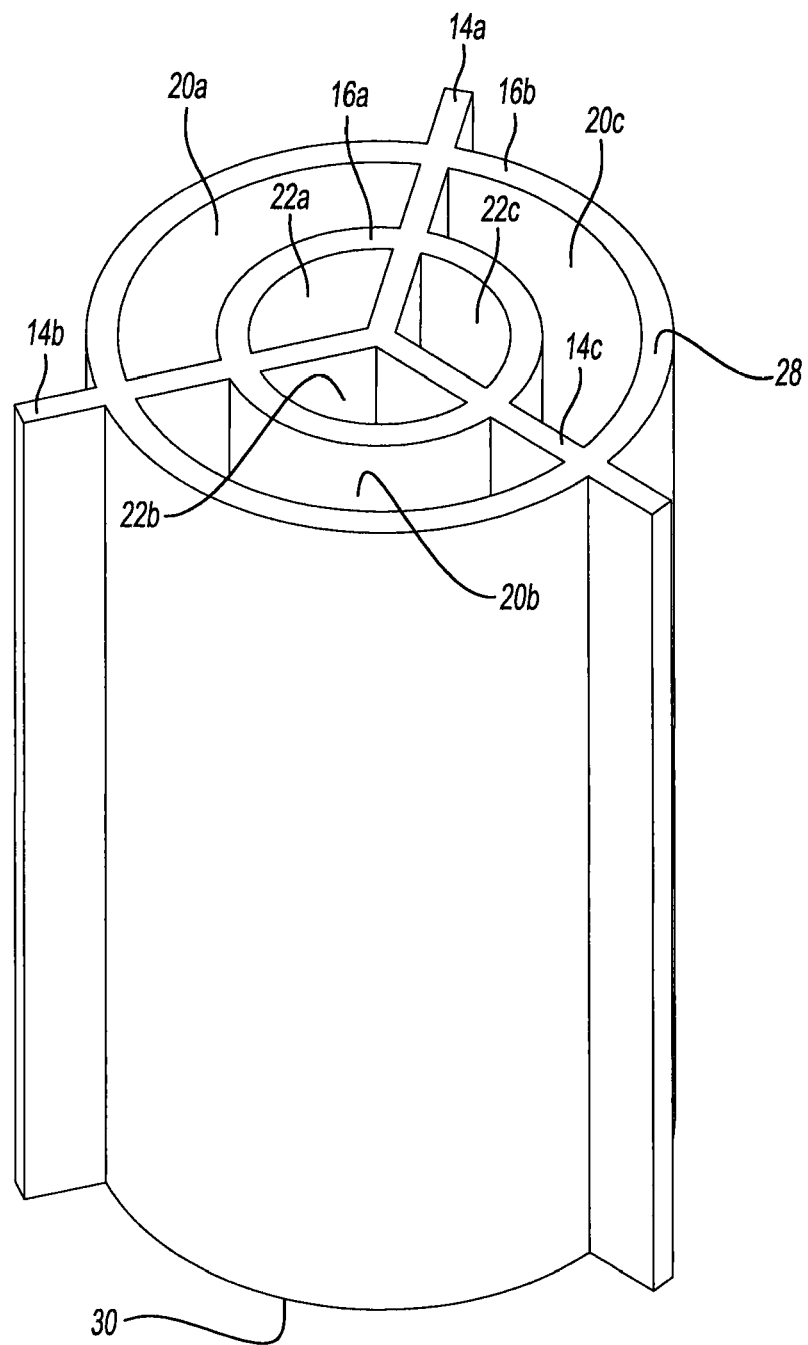
FIG. 1A is a top perspective view of a funnel in accordance with one embodiment of the present disclosure.
Figure 1B:
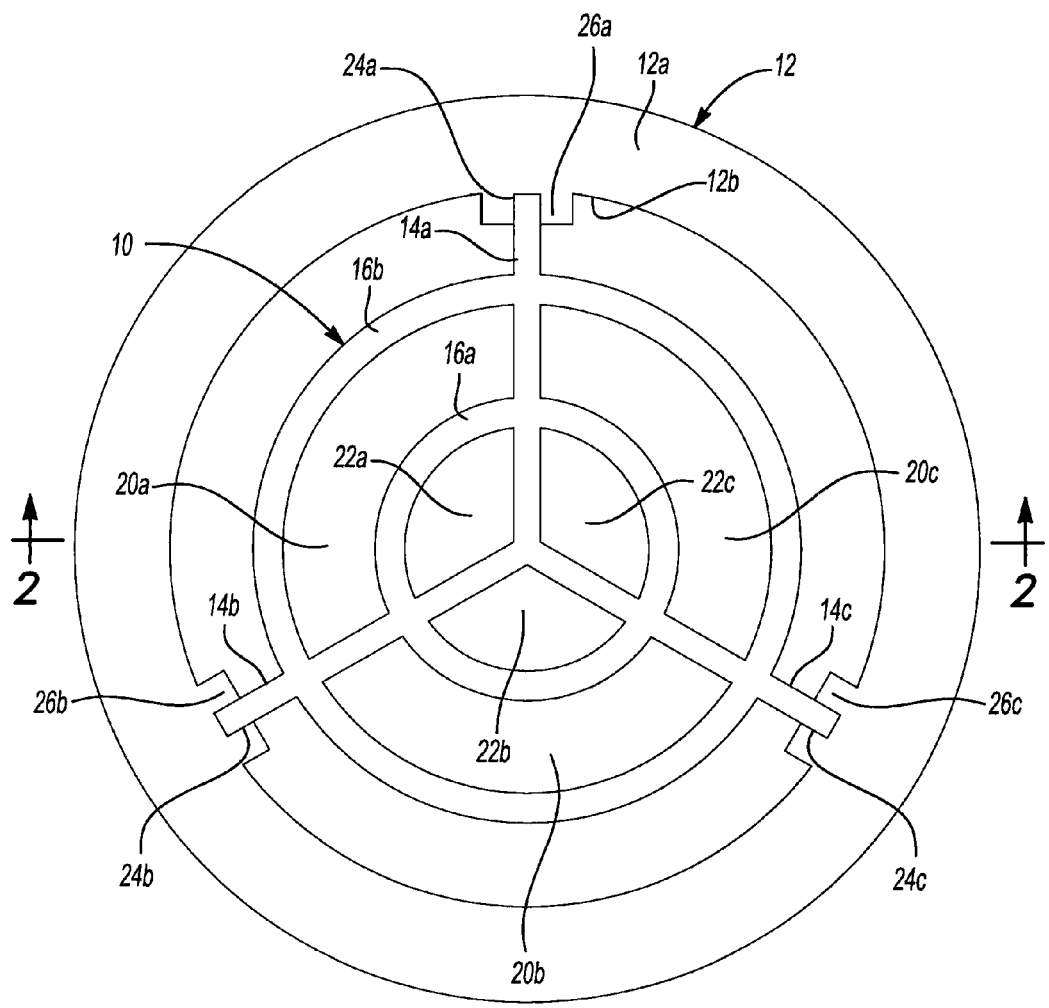
FIG. 1B is an plan view of the funnel of FIG. 1A.

Referring to FIG. 1, a funnel apparatus 10 is shown in one embodiment of the present disclosure. The funnel apparatus 10 (hereinafter simply "funnel 10") is well suited for use in applying individual cells, or groups of cells, to one or more predefined regions on a seeding or physical growth surface. The seeding or physical growth surface may be contained in a petri dish, the surface of an electrode, or any physical surface where one desires the cell (or cells) to be able to survive and multiply.

The funnel 10, in one example as shown in FIG. 1, is configured to be temporarily positioned over and aligned with a culture well 12. More specifically, the funnel 10 may be temporarily positioned over, so as to rest on, or just slightly above, a seeding surface 32 (FIG. 2) of a culture well 12. The funnel 10 is also able to be temporarily secured to the culture well 12 in a predetermined angular relation to various predetermined surface portions of the seeding surface of the culture well.

The funnel 10 in this example has a body 11 which includes radially extending wall portions 14a-14c that meet at their radially inward most ends at an axial center of the funnel. Circumferential wall portions 16a-16b intersect the radially extending wall portions 14a-14c. The wall portions 14a-14c, 16-16b and an inner surface 12b of an outer wall portion 12a of the culture well 12 combine to produce a plurality of distinct, independent flow paths 20a-20c and 22a-22c. In this example flow paths 20a-20c form generally arcuately shaped flow paths, and flow paths 22a-22c form generally pie shaped flow paths. The flow paths 20 and 22 are further arranged concentrically in this example.

To achieve precise alignment of the funnel 10 relative to the culture well 12, a plurality of notches or grooves 24a-24c may be formed in radially inwardly extending portions 26a-26c of the culture well 10. The grooves 24a-24c receive the radially extending wall portions 14a-14c. In this manner the angular orientation of the funnel 10 relative to the culture well 12 can be precisely set. When different cells are being seeded onto specific surface regions of the seeding surface 32 (FIG. 2) of the culture well 12, the angular alignment of the funnel 10 relative to the culture well 12 and the seeding surface regions will be highly important.

Figure 2:
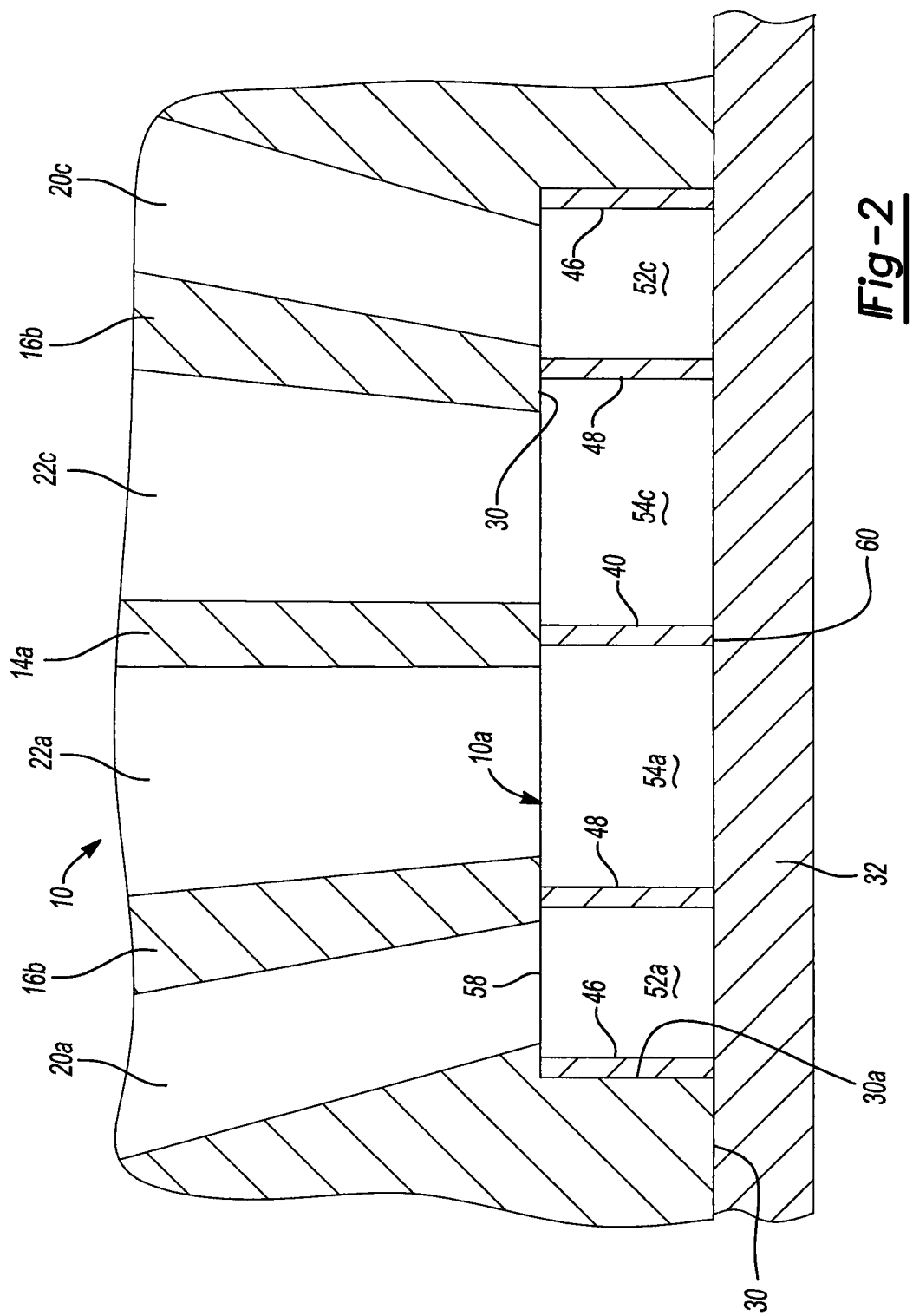
FIG. 2 is a side cross sectional view in accordance with section line 2-2 in FIG. 1B of the funnel positioned over a lower funnel, with the lower funnel resting on a planar seeding or physical growth surface.

Referring to FIG. 2, a portion of the funnel 10 is shown in cross section to illustrate that the flow paths 20a-20c and 22a-22c may each having a decreasing cross section area going from an upper surface 28 (shown in FIG. 1A) of the funnel 10 to its lower surface 30 (shown in FIG. 1A). In FIG. 2, only flow paths 20a, 22a, 22c and 20c are shown. The funnel 10 may be formed from a 3D printing process from any biocompatible plastic suitable for use with a 3D printing process. Examples of suitable materials are polycarbonate (PC), polycarbonate ISO (PS-ISO), MED610, ABS-M30i, just to name a few.

FIG. 2 also shows the funnel 10 being used with a separately manufactured lower funnel apparatus 10a (hereinafter simply "lower channeling apparatus 10a") which the funnel 10 rests on. The funnel 10a is a microfabricated component which may be made using a well known wafer level photolithographic process by which its flow paths are formed by etching. The use of the photolithographic process enables flow path wall portions for the lower funnel 10 to be formed which are significantly thinner in cross section, and which enable the spacings between surface regions on the seeding surface 32 to be significantly reduced, for example to just a few microns. Such minimal spacing would be impossible to achieve using present day 3D printing processes.

Figure 3:
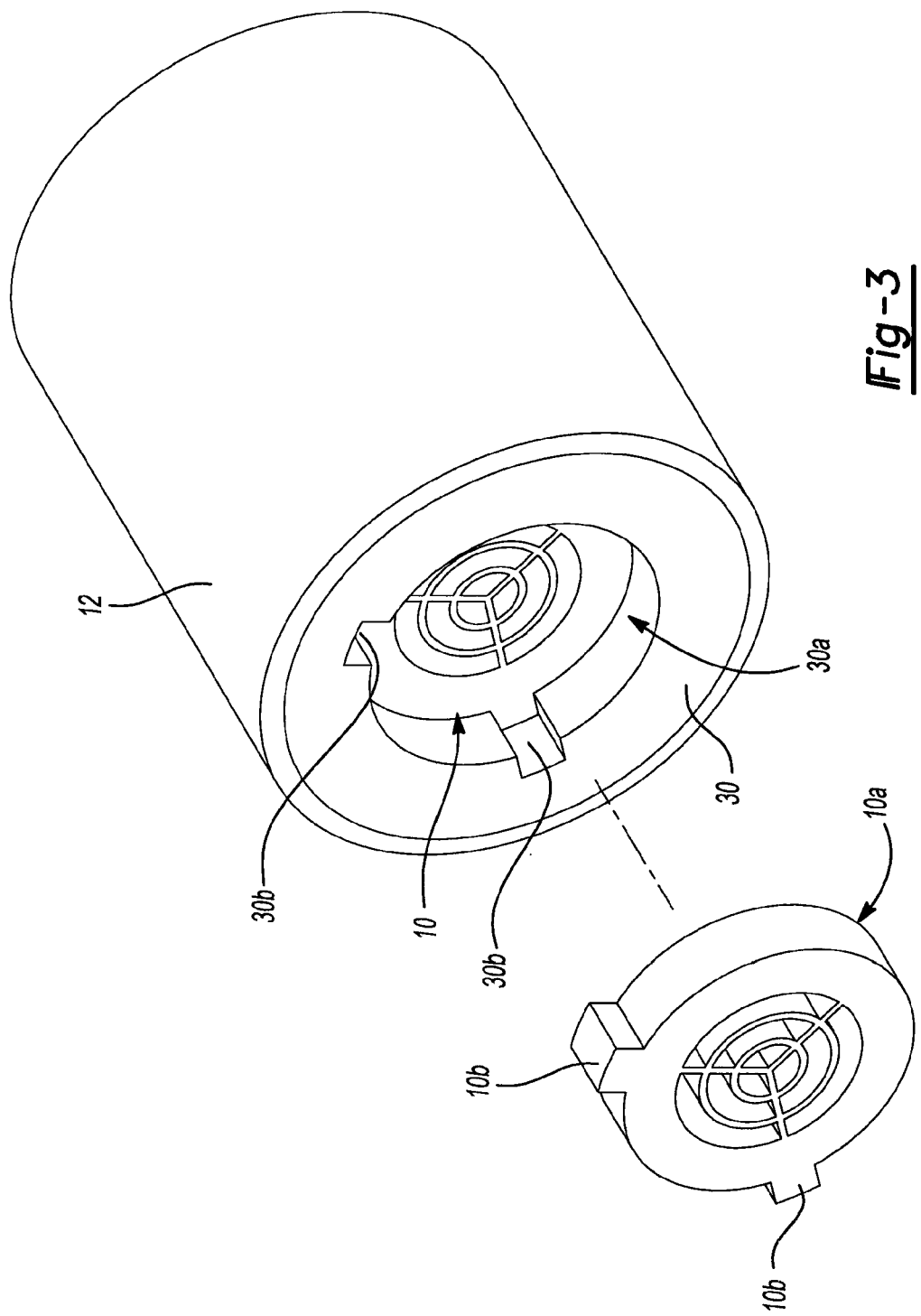
FIG. 3 is an exploded perspective view showing the lower funnel spaced apart from the bottom surface of the upper funnel.

The funnel 10a essentially forms an extension of the funnel 10 to enable cells, or groups of cells, to be deposited into even more closely spaced regions than would be possible using just the funnel 10. As can be seen in FIG. 2, the lower surface 30 of the funnel 10 overhangs the perimeter of the lower channeling apparatus 10a slightly to ensure that cells travelling down the flow paths 20a, 22a, 22c and 20c are directed completely into the corresponding flow paths in the lower channeling apparatus 10a. This feature will be described in more detail in the following paragraphs. Referring further to FIGS. 2 and 3, the bottom area of the funnel 10 and the lower channeling apparatus 10a can be seen in additional detail. In this view the seeding surface 32, which essentially forms a bottom wall of the cell culture well 12, has been omitted to show additional features of the interior of the cell culture well 12. The lower channeling apparatus 10a rests directly on the seeding surface 32, which in this example contains an array of electrodes having an upper surface coated with a suitable cell growth supporting coating such as Polylycine. However, the seeding surface 32 could be any suitable media or material capable of receiving and allowing the growth of cells deposited thereon.

FIG. 2 shows the funnel 10 positioned in the cell culture well 12, and with the lower channeling apparatus 10a disposed in a main recess 30a in the lower surface 30 of the funnel 10. FIG. 3 shows the lower channeling apparatus 10a spaced apart from the lower surface 30 of the funnel 10. To facilitate alignment of the lower channeling apparatus 10a relative to the funnel 10, the main recess 30a may include one or more radially extending notches 30*b* in which alignment tabs 10*b* extending radially outwardly from the lower channeling apparatus 10*a* engage in when the lower channeling apparatus 10*a* is positioned properly within the main recess 30*a*.

In one example the diameter of the cell culture well 12 is about 1 cm in diameter, although it will be appreciated that the diameter, and even the cross sectional shape, of the cell culture well 12 can be varied as needed and need not necessarily be circular. The significantly greater cross sectional area of each flow path 18, 20 and 22 at the upper edge 28 of the funnel 10 allows instruments such as a micropipette to be easily used to manually deposit cells into selected ones of the flow paths 18, 20 and/or 22, for placement into extremely closely spaced regions on the surface of the planar media 36.

Figure 4:
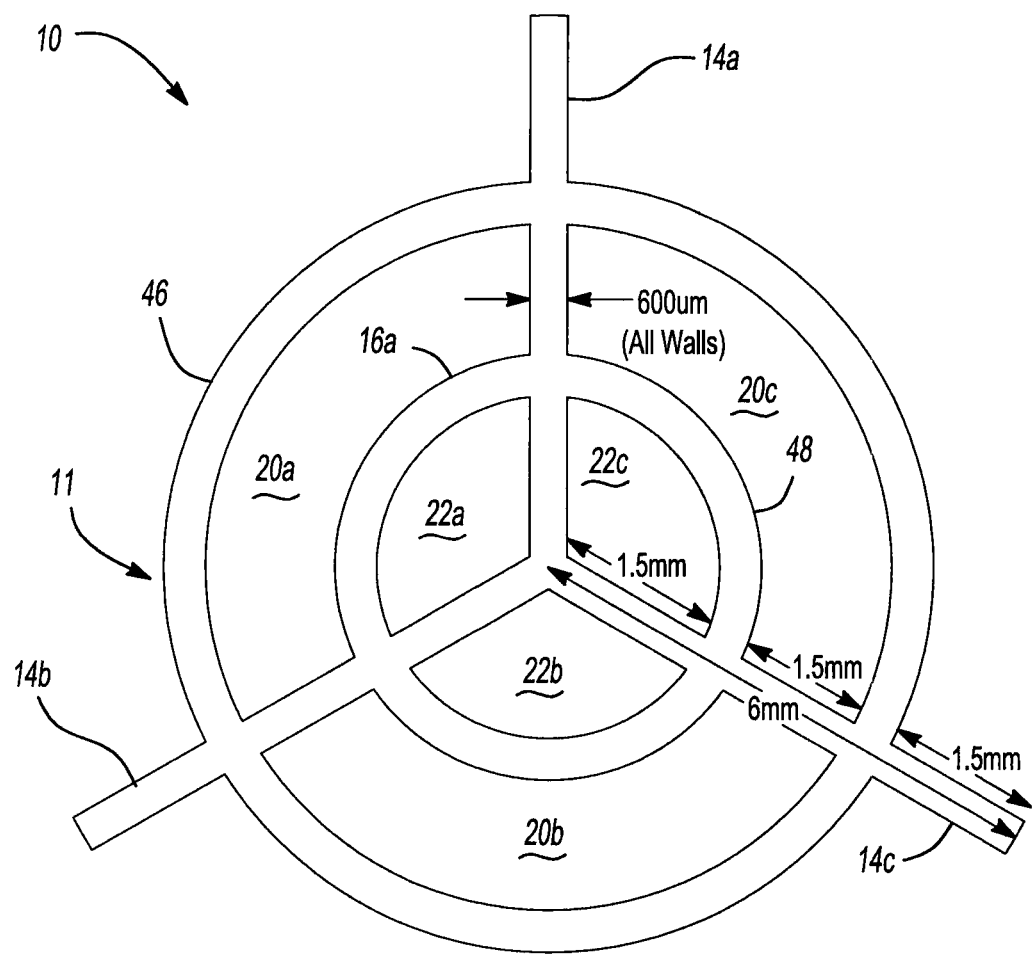
FIG. 4 is a plan view of an upper surface of the funnel illustrating one example of various dimensions that the funnel may have.

Referring to FIG. 4, one example of various possible dimensions for the funnel 10 and its flow paths 18, 20 and 22 is shown. It will be appreciated immediately, however, the funnel 10 can be made with any suitable dimensions, and the precise dimensions of the flow paths 18-22 will be dictated primarily by the dimensions and spacings between the regions of the planar media 36 onto which cells need to be deposited.

Figure 5:
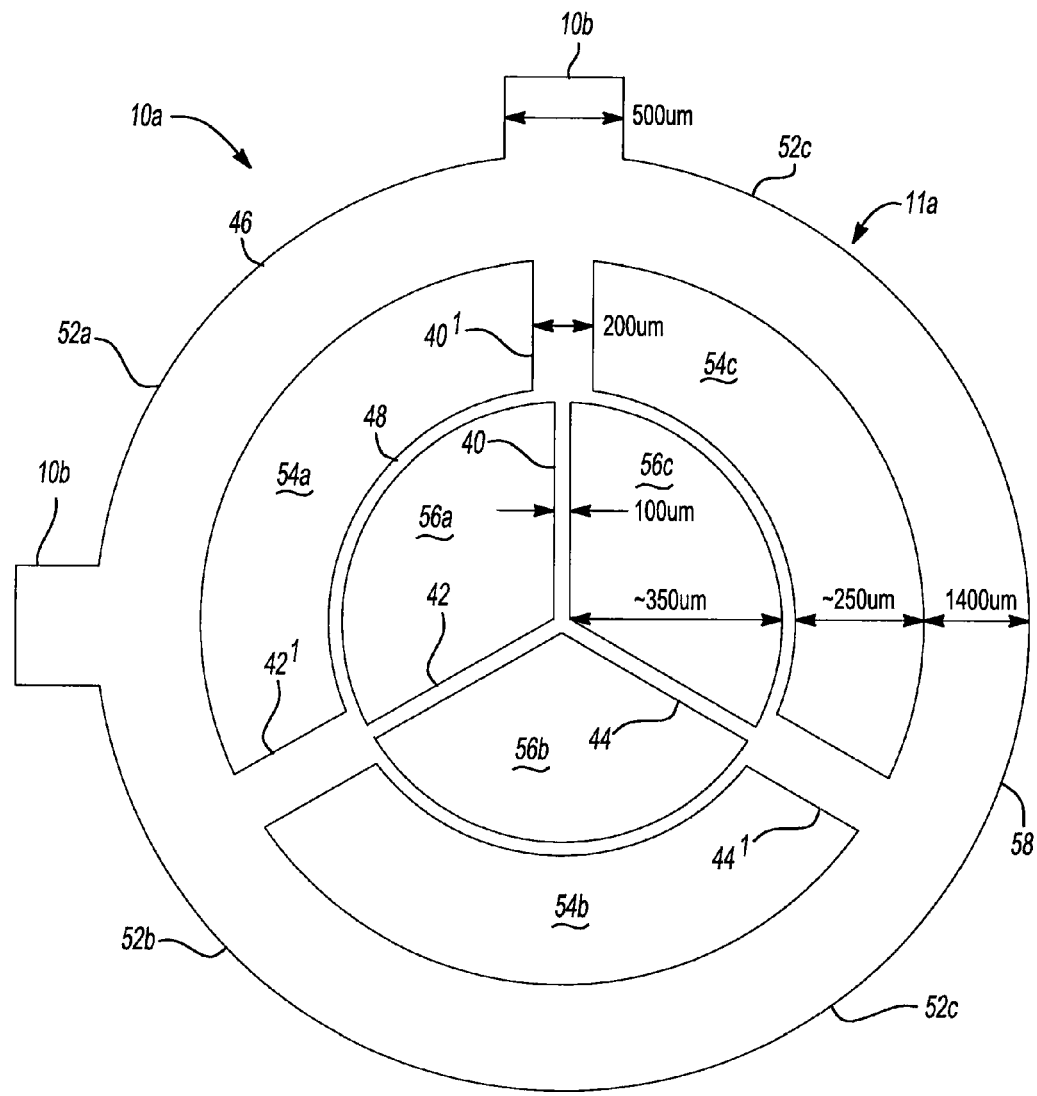
FIG. 5 is a plan view of an upper surface of the lower funnel illustrating one example of various dimensions that the funnel may have.

Referring to FIG. 5, an overhead plan view of the lower channeling apparatus 10*a* can be seen. The lower channeling apparatus 10*a* in this example has a body portion 11*a* which is constructed with radially extending wall portions 40, 42 and 44 which intersect with circumferential wall portions 46 and 48. These intersecting wall portions 40-48 form flow paths 52*a*-52*c*, 54*a*-54*c* and 56*a*-56*c*. Certain ones of the flow paths are also shown in FIG. 2. The dimensions shown in FIG. 5 are merely to illustrate one example of various dimensions that the flow paths 52-56 may have at the upper surface 58 of the lower channeling apparatus 10*a*. In practice, the precise dimensions selected will typically be dependent in part on the dimensions of the flow paths 18, 20 and 22 at the lower surface 30 of the funnel 10. As can be seen in FIG. 2, each of the flow paths 52*a*, 52*c*, 54*a*, and 54*c* (as well as flow paths 52*b*, 54*b* and 56*a*-56*c*, which are not visible in FIG. 2) are formed by wall portions which extend from the upper surface 58 towards a lower surface 60 of the funnel 10*a*, and which have a significantly reduced thickness as compared to the thicknesses of the wall portions of the funnel 10.

The flow paths 52-56 essentially form extensions of flow paths 20 and 22, respectively. The dimensions and spacings of the wall portions 40-48 are selected to essentially form an extension of the funnel 10 so that the flow paths 52-56 enable cells to be channeled into even more closely spaced regions on the seeding surface 32 than what would be possible using just the funnel 10.

While the flow paths 20 and 22 in this example all have a generally uniformly decreasing cross-sectional area from the upper surface 28 to the lower surface 30, it will be appreciated that the funnel 10 need not be constructed such that all of its flow paths 20 and 22 have such a uniformly decreasing cross-sectional area configuration. Certain ones of the flow paths 20 or 22 may be shaped (from a cross-sectional perspective) such that they deposit cells onto regions of the seeding surface 32 which are of different cross sectional areas and/or different cross-sectional shapes. As such, certain ones of the flow paths 20 or 22 may be shaped to channel cells into an arcuately shaped region, while other ones of the flow paths may deposit cells into circular shaped cross-sectional regions, square shaped cross sectional regions, or virtually any other cross sectional shape.

The present disclosure addresses all of the aforementioned shortcomings in with an easy to use apparatus that does not suffer from the shortcomings of prior devices and methods for selectively seeding cells on a permanent physical growth surface. The apparatus of the present disclosure, when used either with just funnel 10 or as a combination of funnels 10 and 10*a*, allows for multiple cell types to easily be seeded into macroscale openings at the top of the funnel 10, then the openings narrow substantially such that the cells land on the surface separated by distances as small as several microns. Once the cells attach, the funnel 10 (or the assembly of funnels 10 and 10*a*) is/are removed, producing a flat, unmodified surface with cells of one or more types localized to specific regions of the substrate.

The funnel apparatus of the present disclosure is expected to find utility in a number of research/development applications involving neuronal communication, microelectrode arrays (MEA), cell migration, cancer metastasis, quorum sensing, growth factor effects, organ-on-a-chip, human-on-a-chip, tissue engineering, and developmental biology, just to name a few likely applications.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A funnel apparatus for channeling cells in a flowable medium onto a plurality of distinct, closely spaced regions of a seeding surface through the funnel apparatus, the funnel apparatus comprising:
   a body portion having an upper surface and a lower surface;
   the body portion forming a plurality of arcuate flow paths formed in a generally concentric arrangement about an axial center of the funnel apparatus, the flow paths all converging toward the axial center, and at least one of the arcuate flow paths being shaped to have a decreasing cross-sectional area from the upper surface to the lower surface; and
   wherein the arcuate flow paths are formed at the lower surface to enable cells deposited into the flow paths at the upper surface of the funnel apparatus to be channeled into a plurality of distinct, closely spaced regions on the seeding surface positioned adjacent the lower surface.

2. The funnel apparatus of claim 1, wherein each of the arcuate flow paths has a decreasing cross sectional area from the upper surface to the lower surface of the body portion.

3. The funnel apparatus of claim 1, wherein the plurality of arcuate flow paths are formed by:
   at least a plurality of radially extending wall portions; and
   at least one circumferential wall portion that intersects the plurality of radially extending wall portions.

4. The funnel apparatus of claim 3, wherein at least one of the plurality of arcuate flow paths has a pie shape.

5. The funnel apparatus of claim 4, wherein the plurality of arcuate flow paths includes first and second groups of concentrically arranged, arcuately shaped flow paths, and wherein all of the arcuate flow paths converge uniformly toward the axial center of the funnel apparatus.

6. The funnel apparatus of claim 5, wherein the funnel is made from at least one of:
polycarbonate (PC);
polycarbonate ISO (PS-ISO);
MED610; or
ABS-M30i.

7. The funnel apparatus of claim 2, further comprising a lower channeling apparatus having an additional plurality of flow paths formed therein, and configured to be positioned against the lower surface of the body portion so as to be positioned between the lower surface and the seeding surface, the lower funnel apparatus forming an extension of the funnel apparatus.

8. The funnel apparatus of claim 7, wherein the additional plurality of flow paths of the lower channeling apparatus define reduced thickness wall portions that enable spacings between adjacent flow paths to be further reduced.

9. The funnel apparatus of claim 8, wherein the lower channeling apparatus is made using a photolithographic process.

10. The funnel apparatus of claim 8, wherein the funnel includes a main recessed area having at least one recessed portion; and
wherein the lower channeling apparatus includes at least one radially projecting alignment tab which engages with the at least one recessed portion to key an angular orientation of the lower channeling apparatus to the funnel.

11. A funnel apparatus for channeling cells in a flowable medium through the funnel apparatus onto a plurality of closely spaced regions of a seeding surface, the funnel apparatus comprising:
an upper funnel having:
a body portion, the body portion having an upper surface and a lower surface;
the body portion forming a plurality of arcuate flow paths arranged in a plurality of generally concentric rings about an axial center of the body portion, all of which are shaped to have a decreasing cross-sectional area from the upper surface to the lower surface, and all of which converge to the axial center of the body portion; and
a lower channeling apparatus having:
a body portion having an upper surface and a lower surface;
the body portion positioned such that the upper surface of the lower channeling apparatus rests against the lower surface of the upper funnel; and
the lower channeling apparatus including an additional plurality of flow paths in registration with the plurality of arcuate flow paths of the upper funnel, such that cells deposited into the plurality of arcuate flow paths of the upper funnel flow through the additional plurality of flow paths of the lower channeling apparatus and onto the closely spaced regions of the seeding surface, and wherein the seeding surface is used to support the lower surface of the lower channeling apparatus.

12. The funnel apparatus of claim 11, wherein at least certain ones of the plurality of arcuate flow paths of the upper funnel decrease in cross sectional area from the upper surface of the upper funnel to the lower surface of the upper funnel.

13. The funnel apparatus of claim 12, wherein at least certain ones of the additional plurality of flow paths of the lower channeling apparatus are defined by reduced thickness walls in the lower channeling apparatus which enable the cells to be deposited onto the closely spaced regions of the seeding surface.

14. The funnel apparatus of claim 11, wherein at least one of plurality of arcuate flow paths of the upper funnel forms a first arcuate flow path, and wherein at least one of the additional plurality of flow paths of the lower channeling apparatus forms a second arcuate flow path in registration with the first arcuate flow path.

15. The funnel apparatus of claim 11, wherein the upper funnel includes a main recess in the lower surface thereof, in which the lower channeling apparatus is positioned.

16. The funnel apparatus of claim 15, wherein the main recess includes a recessed area, and the lower channeling apparatus includes a tab dimensioned to engage within the recessed area when the lower channeling apparatus is positioned in the main recess, to thus key the lower channeling apparatus in a predetermined angular configuration relative to the upper funnel.

17. The funnel apparatus of claim 16, wherein the main recess includes a pair of the recessed areas, and the lower channeling apparatus includes a pair of the tabs configured to engage in the pair of the recessed areas.

18. A funnel apparatus for channeling cells in a flowable medium through the funnel apparatus onto a plurality of distinct, closely spaced regions of a seeding surface, the funnel apparatus comprising:
a body portion having an upper surface and a lower surface;
the body portion forming a plurality of flow paths formed in a plurality of generally concentric rings about an axial center of the funnel apparatus, each of the flow paths being shaped to have a decreasing cross-sectional area from the upper surface to the lower surface; and
wherein the flow paths all converge toward an axial center of body portion, and are formed at the lower surface to enable cells deposited into the flow paths at the upper surface of the funnel apparatus to be channeled into a plurality of distinct, closely spaced regions on the seeding surface positioned adjacent the lower surface.

* * * * *